(12) United States Patent
Povel et al.

(10) Patent No.: US 8,315,806 B2
(45) Date of Patent: Nov. 20, 2012

(54) METHOD FOR DETERMINING COLOR PERCEPTION IN MULTILAYER SYSTEMS

(75) Inventors: Kirsten Povel, Hamburg (DE); Hans-Joachim Cappius, Berlin (DE); Gerhard Mueller, Berlin (DE)

(73) Assignee: DeguDent GmbH, Hanau (DE)

( * ) Notice: Subject to any disclaimer, the term of this patent is extended or adjusted under 35 U.S.C. 154(b) by 1162 days.

(21) Appl. No.: 10/585,816

(22) PCT Filed: Jan. 14, 2005

(86) PCT No.: PCT/EP2005/000319
§ 371 (c)(1),
(2), (4) Date: Sep. 22, 2008

(87) PCT Pub. No.: WO2005/068953
PCT Pub. Date: Jul. 28, 2005

(65) Prior Publication Data
US 2009/0182510 A1    Jul. 16, 2009

(30) Foreign Application Priority Data
Jan. 14, 2004  (DE) .................. 10 2004 002 929

(51) Int. Cl.
*G01N 33/48* (2006.01)
(52) U.S. Cl. .................. 702/19; 702/21; 702/33; 703/2
(58) Field of Classification Search .................. 702/19, 702/21, 22, 28, 30, 32; 703/2
See application file for complete search history.

(56) References Cited

U.S. PATENT DOCUMENTS

| | | | |
|---|---|---|---|
| 5,717,605 A | 2/1998 | Komiya et al. | |
| 7,054,674 B2 * | 5/2006 | Cane et al. | 600/407 |
| 2003/0223060 A1 | 12/2003 | Graf et al. | |
| 2005/0255424 A1 * | 11/2005 | Hack et al. | 433/29 |

FOREIGN PATENT DOCUMENTS
DE    19652885    6/1998

OTHER PUBLICATIONS

Shimada et al. "Melanin and Blood Concentration in a Human Skin Model Studied by Multiple Regression Analysis: Assessment by Monte Carlo Simulation," 2001.*
Shimada et al, "Melanin and Blood Concentration in a Human Skin Model Studied by Multiple Regression Analysis: Assessment by Monte Carlo Simulation", Physics in Medicine and Biology vol. 46, No. 9, Sep. 2001, pp. 2397-2406.

* cited by examiner

*Primary Examiner* — Sujoy Kundu
(74) *Attorney, Agent, or Firm* — Dennison, Schultz & MacDonald

(57) ABSTRACT

A method for determining the color perception of multi-layer dispersive materials or biological materials for layer thicknesses that are respectively selective, by the determination of the diffuse reflectance based on the respective intrinsic optical parameter using Monte Carlo simulations and taking into consideration the measurement geometries, anisotropy and the dispersion phase function in order to correctly take into account the multiple internal dispersion of the material. The color effect is calculated from the diffuse reflectance based on the various color systems in accordance with different algorithms.

8 Claims, 4 Drawing Sheets

METHOD FOR DETERMINING COLOR PERCEPTION IN MULTILAYER SYSTEMS

Figure 1:
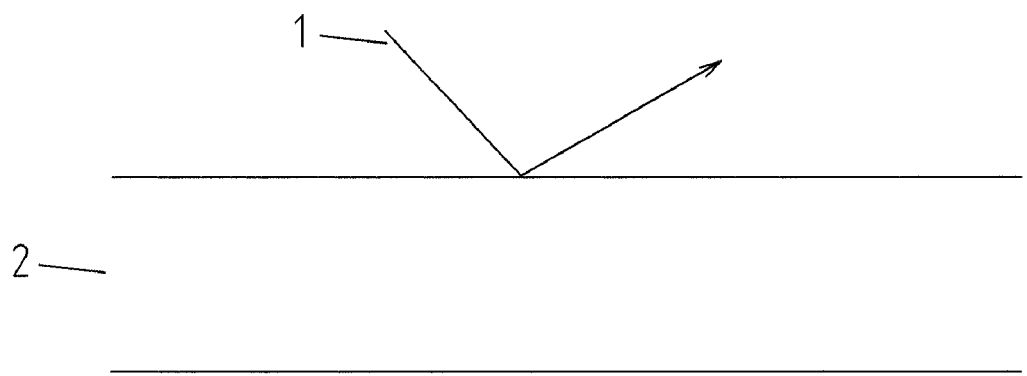

This is a U.S. national phase application of PCT/EP2005/000319, filed Jan. 14, 2005, which claims priority to German Application No. DE 10 2004 002 929.6, filed Jan. 14, 2004, both of which are incorporated herein by reference.

The invention relates to a method for determining the color effect of dispersive materials such as materials or biological substances of a multilayer system, in particular a series of layers in teeth or dental materials.

An objective of determining the color perception is an adaptation or an adjustment of the color effect of new multilayer systems in existing multilayer systems, for example, as a step of quality assurance or when developing and assessing new materials and their combinations. This applies to multilayer systems in the field of cosmetic or aesthetic medical applications, e.g. for dentures, up to technical fields, e.g. for automobile finishes or plastics. The color effect of a material system is dependent on the layer thickness and the back dispersion (remission) of the light and can be determined pursuant to DIN 5033 according to the parity, tristimulus or spectral method for different color systems, e.g. CIELAB or CIELUV. For example, measuring instruments such as color spectrometers or colorimeters can be used as well as a visual sampling, e.g. by means of special color scales as described e.g. for the dental field in DE A 196 46 923, DE-A 101 21 553 or DE-A 100 23 840.

Due to the technical manufacturing process to be carried out in multilayer systems and the combination of individual layers, the color effect cannot be compared directly, but only determined and assessed afterward, i.e. after it has been finished, when it is no longer possible to correct the color.

Therefore, to obtain a desired color effect and determine or predict the respective color effect in varying layer thicknesses, time-consuming and expensive series of measurements and tests by the manufacturer are generally required, also according to the trial and error principle. To avoid this, attempts are being made to calculate the color effect with aid of simulations. This can be accomplished with sufficient accuracy for individual layers and less complex material systems that only have a molecular dispersion due to their relatively homogeneous inner structure.

A calculation of this type for predicting the color effect for different layer thicknesses has thus far been carried out with aid of a Kubelka-Munk equation as a one-dimensional model for solving the radiation transport equation, both in the field of dental science and in the technical field, such as in the paint industry, as basis of, for example, concentration-dependent computer color matching. The absorption coefficient $A_{KM}$ and dispersion coefficient $S_{KM}$ are calculated therewith from transmission or remission properties measured on material samples. The remission spectra for various layer thicknesses can be predicted on the basis of $A_{KM}$ and $S_{KM}$, for example, in front of a white or black background or in front of a background defined according to a color system. The color effect can be calculated from the remission spectra dependent on the color system used. For example, the calculation of the color effect according to CIELAB pursuant to the standard DIN 5033 can be ascertained by converting the remission values into X, Y, Z tristimulus values and subsequently into CIELAB values. This conversion of measured remission values into CIELAB values is also integrated in the software of color spectrometers, as used in the paint industry. By comparing the CIELAB values and calculating the difference in color $\Delta E_{ab}$ pursuant to DIN standard 6074, variations in color between samples of the studied materials can be ascertained.

However, with the Kubelka-Munk equation, the measurement geometries of the measuring apparatus used for the transmission or remission measurements cannot be taken into consideration and simplified assumptions that are detrimental to accuracy can be made. This results in systematic errors which can become apparent in visible differences in color between simulation result and reality. However, the greatest disadvantage of the Kubelka-Munk theory is that only processes of surface reflection can be taken into consideration. For example, this is shown in FIG. 1 on the light path of a photon 1 after reflection of the light on the surface of a material layer 2 of predetermined thickness.

Figure 2:
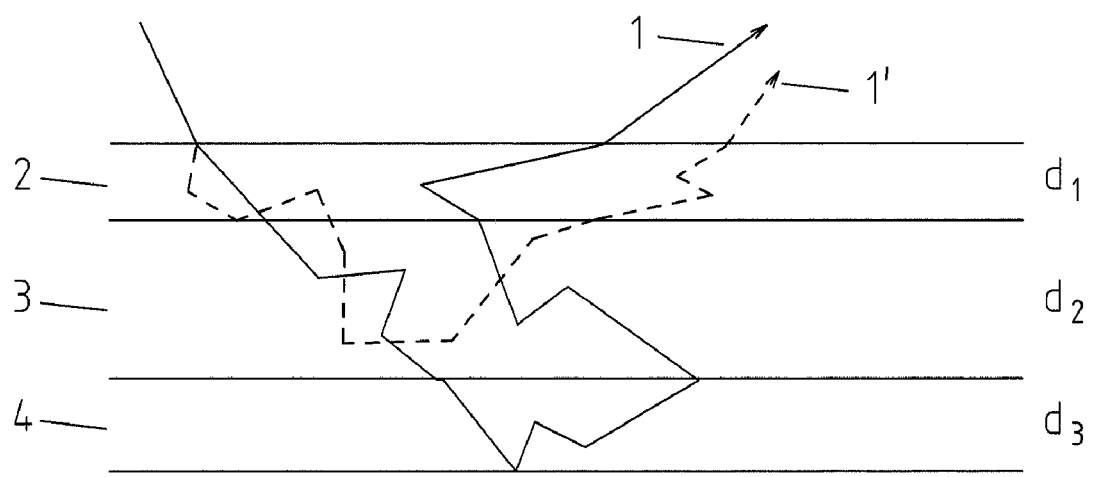

With the Kubelka-Munk equation, the actually existing conditions can no longer be correctly reproduced in multilayer systems in which structural—not molecular—dispersion geometries are present. In this case, due to the layer structure and the structure peculiarities, a light propagation with internal multiple dispersion processes results in the material. The remission and with it the color effect result from a very complex interaction of the optical properties of the different contents and components of the layers due to the light propagation by scattering, absorption and refraction on the boundary layers. By way of example, FIG. 2 shows the light path of a photon 1 and an alternative light path 1' after multiple scatterings within several successive material layers 2, 3, 4 of different thickness and type. Therefore, when using the Kubelka-Munk equation for multilayer systems with structure scattering, essential reservations concerning the accuracy of the prediction of the remission and thus the color effect must be accepted which become noticeable as visually perceivable differences. Therefore, to improve the predictable accuracy of the remission and thus the color effect, the development of a method is required which can correctly and accurately take this structurally-dependent multiple dispersion into consideration.

The object of the present invention is to more accurately than previously be able to calculate and thus predict the color perception for multilayer systems of combinations of various dispersive materials or biological substances consisting of combined, different layers with various optical properties for varying layer thickness without having to repeatedly produce samples consisting of the combined layer thicknesses of interest and to have to measure the color effect, e.g. in conventional color spectrophotometers, in each case.

In particular, the color perception for multilayer systems in the dental field should be calculated or predicted, whereby series of layers in teeth, e.g. enamel and dentine, in any layer thickness desired and dental materials, e.g. composites and ceramics, are of special interest.

To solve the object, the invention essentially provides that the remission of the multilayer system is calculated by means of Monte Carlo simulations based on the respective intrinsic optical parameters of the different materials of the layer system comprising dispersion coefficient $\mu_s$, anisotropy factor g and corrected absorption coefficient $\mu_{ak}$ and including refractive index n, thickness d of the respective layer and dispersion phase function of the individual materials in each case.

The intrinsic optical parameters can thereby be determined based on spectrometric measurements or taken from a data bank.

According to the invention, a method is proposed with which the visual perception of the color of multilayer systems or the results of their measurement detection, e.g. by color spectrometer, can be accurately determined or predicted adequately. Surprisingly, it was shown that, in the presence of structural dispersion geometries in multilayer systems with simulation calculations according to the principle of the Monte Carlo simulation as three-dimensional solution approach of the radiation transport equation and a subsequent special correction process, a more correct and essentially accurate determination of the color perception is possible than previously.

The optical properties of the respective materials or biological substances contained in the multilayer system serve as initial data in the form of intrinsic optical parameters absorption coefficient $\mu_a$, dispersion coefficient $\mu_s$ and anisotropy factor g.

To determine the intrinsic optical parameters—also called microscopic parameters—which are independent of the material thickness, methods can be used which are known from tissue optics for dosimetric calculations in medicinal laser therapies. Thus, a calculation can be made with aid of an inverse Monte Carlo simulation from the macroscopic optical parameters, such as the diffuse remission $R_d$, the total transmission $T_t$, the diffuse transmission $T_d$ or the collimated transmission $T_c$ which were measured in an Ulbricht sphere-type spectrometer on samples having a previously ascertained suitable sample thickness d.

In particular, it is provided that the intrinsic optical parameters dispersion coefficient $\mu_s$ (uncorrected), absorption coefficient $\mu_a$ and anisotropy factor g of a material based on the macroscopic optical parameters of the material in the form of, in particular, diffuse remission $R_d$, diffuse transmission $T_d$ and/or total transmission $T_t$ and/or the collimated transmission $T_c$, taking the dispersion phase function of the material into consideration, thickness d of a layer of the material used for determining the macroscopic parameters and refractive index n of the material can be calculated by means of inverse Monte Carlo simulation.

After that, the dispersion phase function and the refractive index n of the material can be calculated by means of inverse Monte Carlo simulation of the corrected absorption coefficient $\mu_{ak}$ for each material on the basis of both intrinsic optical parameters dispersion coefficient $\mu_s$ and anisotropy factor go as well as the remission of an optically dense layer consisting of the material, having a thickness $d_D$ and taking into consideration at least the thickness $d_D$. The dispersion coefficient $\mu_s$ and the anisotropy factor g are already known from the previously completed calculation.

In other words, according to the invention, the calculated absorption coefficient $\mu_a$ is corrected with aid of the remission values of an optically denser sample of the test thickness $d_D$ of the material to be studied together with the determined values of $\mu_s$ and g in a renewed inverse Monte Carlo simulation for the corrected absorption coefficient $\mu_{ak}$. The accuracy of the calculation of the color effect is substantially increased by this step.

The absorption can be calculated all the more accurately the greater the thickness of a layer. However, to determine the initial data $\mu_a$, $\mu_s$ and g, no optically dense sample may be used for the spectrometric measurement since a certain percentage of collimated transmission, i.e. transparency, is required for this simulation process.

The data concerning the intrinsic optical parameters can be provided in a data bank in expansion of the basic idea of the invention in dependency on the material. When setting up a data bank of this type which contains the intrinsic optical parameters $\mu_{ak}$, $\mu_s$ and g for different materials or biological substances or dental materials, reference can be made to these values, so that spectrometric measurements are no longer required when using these materials in a multilayer system for determining their color effect.

Subsequently, based on $\mu_{ak}$, $\mu_s$ and g, the remission for a multilayer system can be calculated by a forward Monte Carlo simulation at an selectable wavelength and respectively selectable thicknesses of the layers contained in the multilayer system. Instead of the remission, the calculation of the transmission is also possible. The wavelength-dependent values of the remission can be transformed into color values e.g. the coordinates according to CIELAB or other color systems by means of suitable algorithms. It is also possible to use multifactor analysis to determine the color effect according to new, alternative color systems.

Moreover, it is possible to calculate the color effect for different and freely selectable measurement geometries.

The color effect can thus be determined with the described procedure with a much higher accuracy than previously for a multilayer system as a combination of various materials or biological substances of, in particular, dental or dentotechnical series of layers for varying layer thicknesses of the individual layers since, on the one hand, the multiple scatterings produced by the internal structure dispersion in the different layers can be correctly calculated and, on the other hand, the accuracy further increased by the determination of the corrected absorption coefficient $\mu_{ak}$. In this way, it is possible to predict the color effect for multilayer systems so accurately that visual differences can no longer be perceived. As a result, with known material behaviour, the color effect of a multilayer system can already be precisely predicted for selectable layer thickness combinations prior to production of said multilayer system. Moreover, the measuring geometry can be taken into consideration and thus also the result of layer thickness-dependent measurements in different spectrometers, for example, of remission measurements in color spectrometers, can be predicted.

The method is especially suitable for use in multilayer systems in dentistry to determine the color of dental restoration materials and tooth color in which an especially high accuracy is required due to the very fine color gradations of e.g. reddish, yellowish or greyish white. Both teeth and dental prosthesis materials show a layer structure and complex inner dispersion geometries due to their structural composition. Teeth consist of the hard tooth substances enamel and dentine with prism or tubular structure. Dental prosthesis materials are also composed of layers of varying opacity to duplicate the resultant optical impression for an optimal aesthetic with a complex structure consisting of filling materials of the most varied types and forms which are embedded in a matrix.

The described method which is distinguished by the calculation of the remission for multilayer systems with successive different material layers of selectable layer thickness and properties takes place by means of Monte Carlo simulations based on the intrinsic optical parameters having a corrected absorption coefficient $\mu_{ak}$, dispersion coefficient $\mu_s$ and anisotropy factor g as well as the refractive index n and including the dispersion phase function for considering the internal multiple material dispersion can also be used on all other multilayer systems with structural scatter, both in the biological and technical fields or in other systems. The color effect of e.g. layers which do not extend in a straight but in a curved plane can also be calculated or predicted thereby.

Further details, advantages and features of the invention can be found in the claims, the features found therein—alone and/or in combination—and also in the following description of the embodiments found in the drawings, showing:

FIG. 1 a schematic representation of a light path after surface reflection on a material layer, FIG. 2 schematic representation of light paths in material layers, FIG. 3 a basic representation of a test room with an Ulbricht sphere, FIG. 4 a flow diagram for calculating intrinsic optical parameters, FIG. 5 a flow diagram for inverse Monte Carlo simulation, and FIG. 6 a flow diagram for calculating the remission and subsequently the color effect of a multilayer system.

According to the invention, to determine the color effect of dispersion layers of different materials on the basis of remission spectra, intrinsic (microscopic) optical parameters absorption coefficient $\mu_a$, dispersion coefficient $\mu_s$ and anisotropy factor g of the materials, whether due to calculations on the basis of experimentally ascertained macroscopic optical parameters or taking values found in data banks into consideration, on the basis of which Monte Carlo simulations are carried out. The Monte Carlo simulation is a numerical method with high accuracy used for solving equation systems and statistical processes.

In this way, intrinsic optical parameters can be calculated on the basis of measured macroscopic optical parameters by means of an inverse Monte Carlo simulation with aid of e.g. a simulation software WinFit 32, Version 5.2. developed by Roggan. To measure the macroscopic optical parameters, an Ulbricht sphere-type spectrometer in the form of a double-beam spectrometer can be used, as found in principle in FIG. 3.

Figure 3:
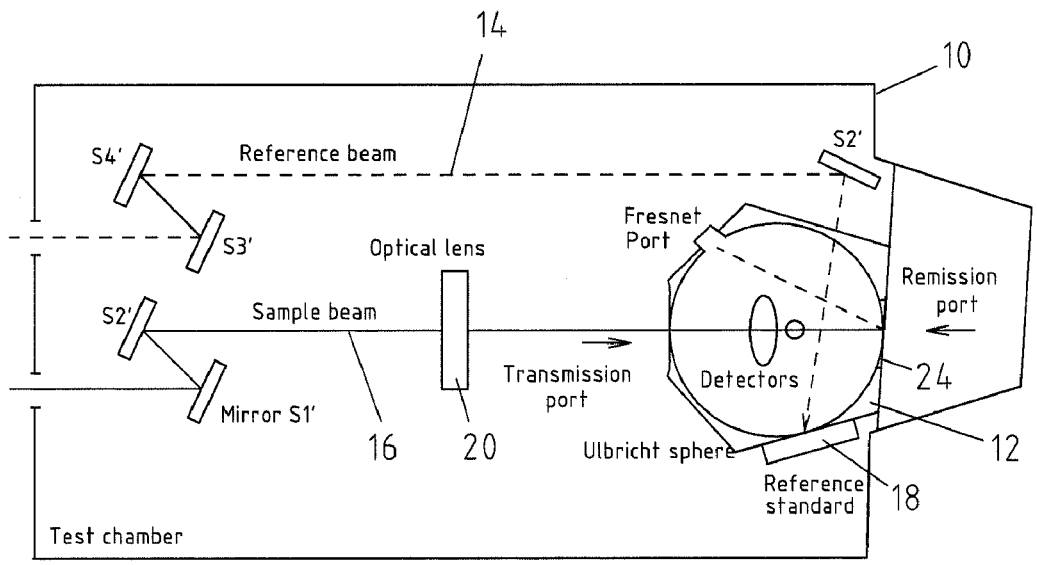
Figure 4:
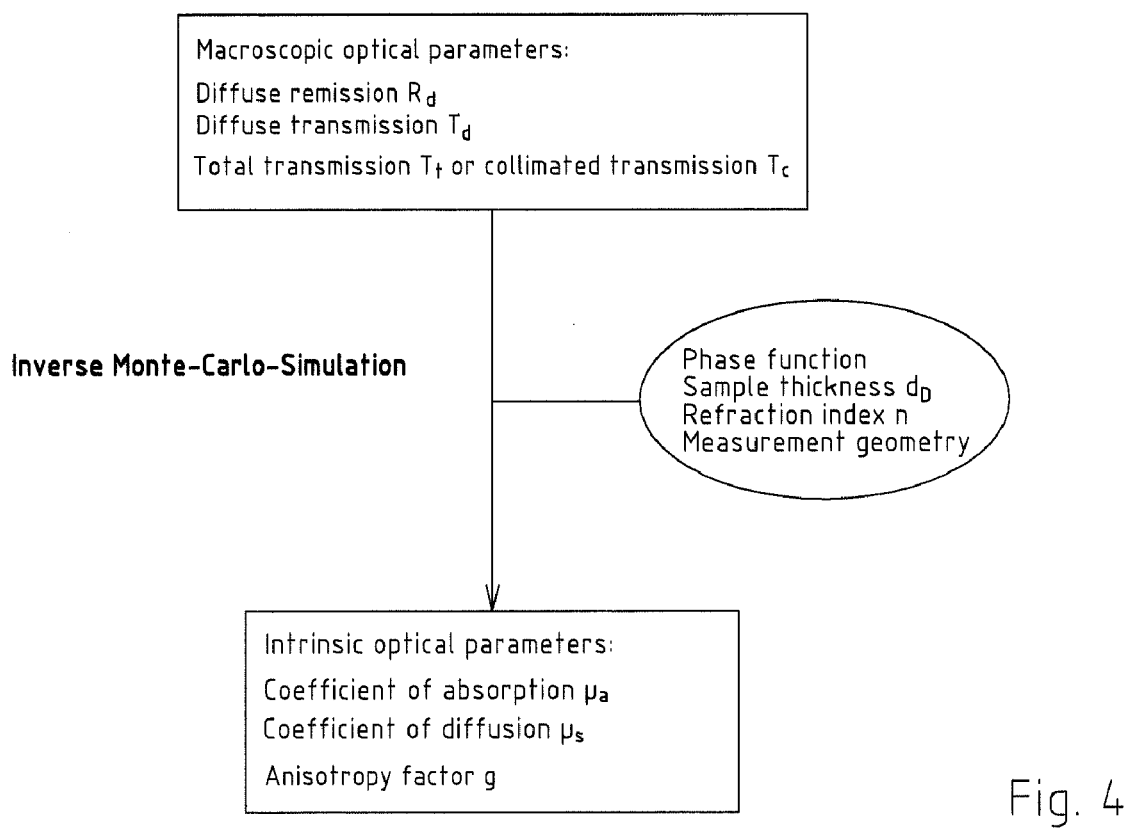

Thus, a test room 10 is shown in FIG. 3 in which an Ulbricht sphere 12 is arranged. Furthermore, reference beam 14 and test beam 16 are drawn in. The reference beam 14 is led via mirror S3', S4' and S5' into the Ulbricht sphere 12 to calibration to a reference standard 18. The Ulbricht sphere 12 and reference standard 18 can consist of spectralon, as a result of which a 99.8% reflection of the light is possible for an almost loss-free detection of the photons.

Via Mirrors S1' and S2', the test beam 16 reaches a test piece (not shown) having a thickness d and into the Ulbricht sphere 12 after having passed through a selectable beam-focussing optical lens 20. The measured values are standardized by the successive emission of a test beam 16 and reference beam 14 automatically with each measured value. The name double-beam spectrometer results from this.

The test piece is fastened in the sample holder either at the transmission port 22 or at the remission port 24 of the Ulbricht sphere 12, dependent on whether or not forward or backward dispersion is to be measured. The respectively selected optical lens 20 regulates the focussing of the light spot on the transmission and remission port 22, 24.

The macroscopic optical parameters diffuse remission $R_d$, diffuse transmission $T_d$ and total transmission $T_t$ can then be measured with a corresponding arrangement. Alternatively, when using another correspondingly constructed Ulbricht sphere-type spectrometer—or an experimental structure with an Ulbricht sphere—in addition to $R_d$ and $T_t$, the collimated transmission $T_c$ can also be measured instead of the diffuse transmission $T_d$. The corresponding macroscopic optical parameters are defined as follows. When a ray of light hits, a distribution of the photons which is specific for the respective medium forms in the radiation volume. A part of the radiation is absorbed. A further part of the photons is scattered in the medium. The dispersion can be subdivided into back dispersion as diffuse remission $R_d$ and forward dispersion as diffuse transmission $T_d$. With a thin layer thickness, photons are also transmitted without a prior dispersion as collimated transmission $T_c$. The sum of collimated and diffuse transmission produces the total transmission $T_t$ ($T_d + T_c = T_t$). These macroscopic parameters are dependent on wavelength, material and layer thickness.

For materials which are used in layer systems, corresponding macroscopic optical parameters are determined. The intrinsic optical parameters of the material, i.e. absorption coefficient $\mu_a$, dispersion coefficient $\mu_s$ and anisotropy factor g, are then determined by inverse Monte Carlo simulation from the macroscopic optical parameters diffuse remission $R_d$, diffuse transmission $T_d$ and/or total transmission $T_t$ and/or collimated transmission $T_c$—two of the transmission parameters must be known ($T_d + T_c = T_t$). In the inverse Monte Carlo simulation, dispersion phase function of the material, test thickness d of the material, refractive index n of the material and measurement geometry are thereby taken into consideration.

When using an Ulbricht sphere-type spectrometer, measurement geometry means e.g. sample geometry, diaphragm diameter, sphere parameter, beam divergence and diameter of the light spot. In other words, existing geometric and optical conditions are taken into consideration in the simulation during measuring, so that systematic errors are avoided and the accuracy of the simulation is increased. In particular, by taking measurement geometry into consideration, e.g. lateral losses of photons on the surface area of the test piece can also be included.

A clear determination of the intrinsic optical parameters requires the measuring of three independent values such as $R_d$, $T_t$ and $T_c$ or $T_d$.

The Heney-Greenstein phase function or the Reynolds-McCormick phase function can be used as dispersion phase function. Other suitable dispersion phase functions, which are typical for the respective material, may also be considered.

In addition to a mathematical formula, the dispersion phase function may also consist of a "look up table", i.e. determination of the dispersion probability via the angle between the direction of the photon to the dispersion occurrence and the direction after the scattering. As a result, a suitable dispersion phase function can be determined for each material. A dispersion phase function may by all means be suitable for several materials, i.e. not be definitely restricted to one material. For example, the Heney-Greenstein function is usually used for a number of biological tissues. However, when g is especially high, it may be advantageous to use the Reynolds-McCormick function.

Figure 5:
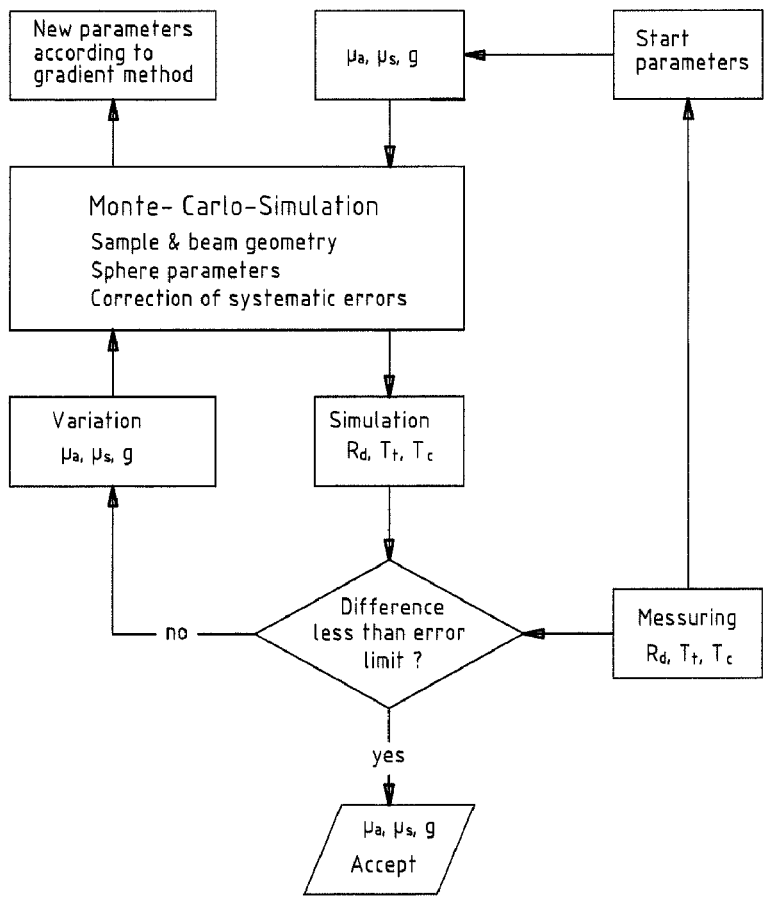

The inverse Monte Carlo simulation can again be found in FIG. 5. In principle, the inverse Monte Carlo simulation works in such a way that one proceeds from intrinsic optical parameter values which are then calculated back to the measured or available macroscopic optical parameters. If a difference results that is smaller than an error limit, then the basic intrinsic optical parameters are accepted.

The intrinsic optical parameters can be determined accordingly to suitable materials.

If, for example, the remission and thus the color effect of a system according to FIG. 2, comprising three different material layers 2, 3, 4, is to be determined, i.e. predicted, the intrinsic optical parameter of each material is then taken as a basis for a forward Monte Carlo simulation. Furthermore, during this simulation, the measurement geometries both for each material the dispersion phase function of each material and the refractive index n of the materials are taken into consideration. Furthermore, the thicknesses $d_1$, $d_2$, $d_3$ of the layers 2, 3, 4 are entered. The thickness of each layer per se is thereby constant.

A wavelength-dependent remission then results from the forward Monte Carlo simulation, the color effect, i.e. the color values according to a selected color system such as CIELAB, are then calculated from said remission by appropriate calculation algorithms or multifactor analysis.

To obtain greater accuracy, it is provided according to the invention that the absorption coefficient be corrected; since with the measurements performed according to FIG. 3, the test pieces must have a thickness that enables a transmission of light. However, the absorption can be determined all the more accurately the greater the thickness of a layer. Therefore, the dispersion coefficient $\mu_s$ and the anisotropy factor g, which were calculated by means of inverse Monte Carlo simulation according to FIGS. 4 and 5, as well as the remission of an optically dense test piece having a thickness $d_D$ are subjected to a further inverse Monte Carlo simulation on the basis of which a corrected absorption coefficient $\mu_{ak}$ is now determined. During simulation, dispersion phase functions of the material, sample thickness $d_D$, refractive index n of the material and the measurement geometry are also taken into consideration. This can be seen in the upper part of FIG. 6.

Figure 6:
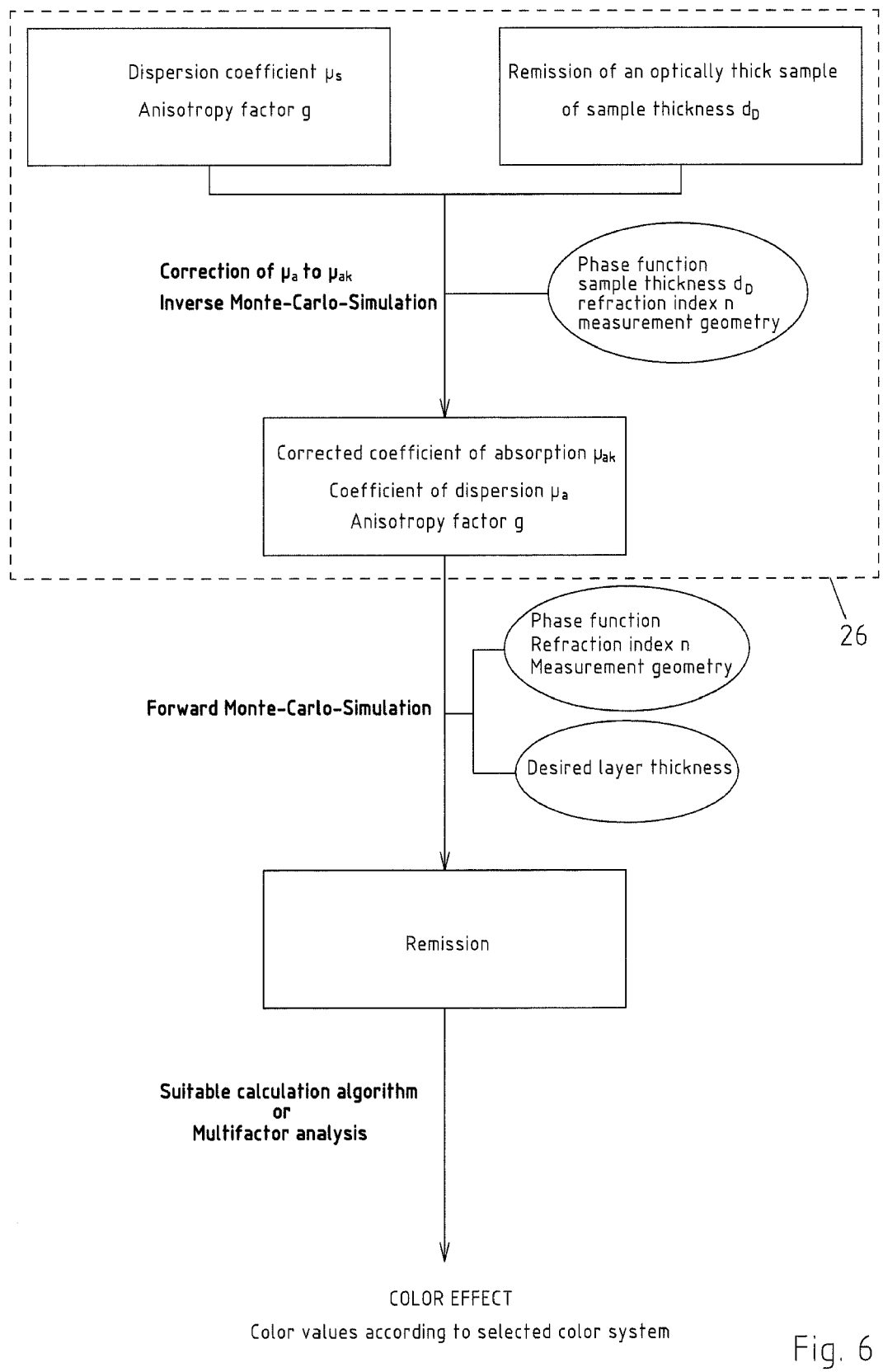

Consequently, for a multilayer system, the calculation shown in principle in the area 26 of the flow diagram of FIG. 6 is performed according to the number of layers or different materials in order to then calculate the remission of the layer system by forward Monte Carlo simulation according to previous explanations on the basis of corresponding material-specific intrinsic optical parameters, i.e. corrected absorption coefficient $\mu_{ak}$, dispersion coefficient $\mu_s$ and anisotropy factor g of the materials, whereby the dispersion phase function, refractive index $n_x$ as well as layer thicknesses $d_x$ and number x of layers of the various materials are taken into consideration, optionally also the measurement geometry.

In this way, the remission of the entire system of all layers is calculated in their geometric sequence, so that, as noted, the phase functions and refractive indices of the materials of the layers having the desired thicknesses and number of layers are to be taken into consideration. The color effect then results from the remission according to e.g. DIN 5033 Farbmessung, Part 1-9, Beuth Verlag Berlin, 1979-1992.

LIST OF REFERENCES

1 Light path
1' Alternative light path
2 First material layer
3 Second material layer
4 Third material layer
10 Test room
12 Ulbricht sphere
14 Reference beam
16 Test beam
15', 52', 53', 54', 55' Mirror
18 Reference standard
20 Lens
22 Transmission port
24 Remission port
26 Area of FIG. 6
$\Delta E_{ab}$ Difference in color according to CIELAB
$\mu_a$ Absorption coefficient
$\mu_{ak}$ Corrected absorption coefficient
$\mu_s$ Dispersion coefficient
$A_{KM}$ Kubelka-Munk absorption coefficient
d, $d_1$, $d_2$, $d_3$ Thickness of test piece
$d_D$ Thickness of test piece of an optically dense sample
g Anisotropy factor
n Refractive index
$R_d$ Diffuse remission
$S_{KM}$ Kubelka-Munk dispersion coefficient
$T_c$ Collimated transmission
$T_d$ Diffuse transmission
$T_t$ Total transmission

The invention claimed is:

1. A method for determining the color effect of a series of layers in teeth or dental materials, wherein the remission of the multilayer system is calculated by means of forward Monte Carlo simulation of intrinsic optical parameters dispersion coefficient $\mu_s$, anisotropy factor g and absorption coefficient of the different materials, calculated by inverse Monte Carlo simulation, taking into consideration refractive index n, thickness d of the respective layer of the materials as well as dispersion phase function of the individual materials and the color effect determined from the remission, characterized in that the intrinsic parameters dispersion coefficient $\mu_s$, anisotropy factor g and absorption coefficient of each of the materials are first calculated on the basis of a layer thickness of material enabling transmission of light and that a corrected absorption coefficient $\mu_{ak}$ is then calculated by inverse Monte Carlo simulation on the basis of the remission of the respective material of an optically dense layer having a thickness $d_D$, the corrected absorption coefficient $\mu_{ak}$ as the absorption coefficient forming the basis for calculating the remission and the color effect of the multilayer system;

wherein the intrinsic optical parameters are determined on the basis of spectrometric measurements.

2. The method according to claim 1, characterized in that the intrinsic optical parameters are taken from a data bank.

3. The method according to claim 1, characterized in that the intrinsic optical parameters dispersion coefficient $\mu_s$, uncorrected absorption coefficient $\mu_a$ and anisotropy factor g of a material are calculated on the basis of macroscopic optical parameters of the material in the form of diffuse remission $R_d$ as well as diffuse transmission $T_d$ and/or total transmission $T_t$ and/or collimated transmission $T_c$, taking into consideration the dispersion phase function of the material, thickness d of a layer of the material used during determination of the macroscopic parameters and refractive index n of the material by means of inverse Monte Carlo simulation.

4. The method according to claim 1,
characterized in that the remission of the layer system is calculated for the series of layers consisting of different materials on the basis of the corrected absorption coefficient $\mu_{ak}$, the dispersion coefficient $\mu_s$ and the anisotropy factor g of each material, taking into consideration at least the dispersion phase function, the refractive index n and thickness d of each layer and series of layers by means of forward Monte Carlo simulation.

5. The method according to claim 1, characterized in that, when calculating the intrinsic optical parameters by means of the inverse Monte Carlo simulation, measurement parameters and/or measurement geometries from the experimental determination of the macroscopic optical parameters are taken into consideration.

6. The method according to claim 1, characterized in that the calculation of the color effect from the remission takes place by means of algorithms or multifactor analysis.

7. The method according to claim 1, characterized in that the color effect is calculated taking the geometric extension such as curvature of the layer system into consideration.

8. The method according to claim 5, characterized in that, when using an Ulbricht sphere-type spectrometer as measurement geometry, test geometry, diaphragm diameter, sphere parameter, beam divergence or diameter of a light spot are used as a basis.

\* \* \* \* \*